United States Patent [19]
Kitajima et al.

[11] Patent Number: 5,996,811
[45] Date of Patent: Dec. 7, 1999

[54] PLASMA COLLECTING DEVICE

[75] Inventors: Masao Kitajima; Akemi Higo, both of Saitama, Japan

[73] Assignee: Fuji Photo Film Co. Ltd., Kanagawa, Japan

[21] Appl. No.: 08/994,420

[22] Filed: Dec. 19, 1997

[30] Foreign Application Priority Data

Feb. 13, 1997 [JP] Japan ......................................... 028652

[51] Int. Cl.⁶ .................................................. B01D 24/26
[52] U.S. Cl. ........................ 210/488; 210/321.6; 210/436; 210/472; 210/489; 210/490; 210/496; 210/500.41; 210/503; 210/506; 210/508
[58] Field of Search ................................ 210/233, 321.6, 210/436, 446, 472, 488, 489, 490, 496, 500.21, 500.41, 503, 504, 506, 508; 422/101, 102, 104; 604/27

[56] References Cited

U.S. PATENT DOCUMENTS

| | | |
|---|---|---|
| 3,260,413 | 7/1966 | Natelson . |
| 3,368,872 | 2/1968 | Natelson . |
| 3,649,505 | 3/1972 | Strickler et al. . |
| 3,663,374 | 5/1972 | Moyer et al. . |
| 3,992,158 | 11/1976 | Przybylowicz et al. . |
| 4,113,912 | 9/1978 | Okita .................................... 428/290 |
| 4,201,548 | 5/1980 | Tamaoku et al. ...................... 422/68 |
| 4,258,001 | 3/1981 | Pierce et al. ........................... 422/56 |
| 4,783,315 | 11/1988 | Arai et al. .............................. 422/56 |
| 4,810,394 | 3/1989 | Masuda ................................ 210/767 |
| 4,879,098 | 11/1989 | Oberhardt et al. .................... 422/101 |
| 4,933,081 | 6/1990 | Sasaki et al. .......................... 210/490 |
| 5,364,533 | 11/1994 | Ogura et al. .......................... 210/645 |
| 5,393,493 | 2/1995 | Makino et al. ........................ 422/56 |
| 5,423,989 | 6/1995 | Allen et al. ........................... 210/650 |
| 5,603,900 | 2/1997 | Clark et al. ........................... 422/101 |
| 5,665,238 | 9/1997 | Whitson et al. ...................... 210/649 |

FOREIGN PATENT DOCUMENTS

| | | |
|---|---|---|
| 0036315 | 3/1981 | European Pat. Off. . |
| 0226465 | 12/1986 | European Pat. Off. . |
| 4-414673 | 6/1969 | Japan . |
| 5-2100783 | 8/1977 | Japan . |
| 5-612640 | 2/1981 | Japan . |
| 5-616187 | 4/1981 | Japan . |
| 5-686941 | 7/1981 | Japan . |
| 2-105043 | 4/1990 | Japan . |
| 2-208565 | 8/1990 | Japan . |
| 4-208856 | 7/1992 | Japan . |
| 8702267 | 4/1987 | WIPO . |

Primary Examiner—John Kim
Attorney, Agent, or Firm—McAulay Nissen Goldberg Kiel & Hand, LLP

[57] ABSTRACT

This invention relates to a plasma-collecting device which comprises a blood filtering material comprising glass fiber filter and microporous membrane, a holder having a blood inlet and a plasma outlet accommodating the blood filtering material, a blood-collecting needle being connected to the blood inlet, and a plasma receiver being provided on the plasma outlet side. The plasma-collecting device can collect a necessary amount of plasma for analysis from blood vessel directly, easily and surely.

8 Claims, 10 Drawing Sheets

PLASMA COLLECTING DEVICE

BACKGROUND OF THE INVENTION

This invention relates to a device for collecting plasma from blood vessel directly by drawing and filtering blood successively.

Type or concentration of blood components, such as metabolites, proteins, lipids, electrolytes, enzymes, antigens, and antibodies, is measured, in general, using a plasma or serum sample obtained by centrifuging whole blood. However, centrifuging takes labor and time. Particularly, centrifuging is unsuitable for an urgent case of measuring a small number of samples promptly and on site inspection, because of requiring a centrifuge and electricity. Thereupon, it has been investigated to separate serum from whole blood by filtration.

Several filtration methods using glass fiber filtration have been known wherein whole blood is charged into the glans fiber in a column from one side of the columns and pressurized or sucked to obtain plasma or serum from the other side (Japanese Patent KOKOKU Nos. 44-14673, 5-52463, Japanese Patent KOKAI Nos. 2-208565, 4-208856).

However, drawing blood and plasma separation are carried out independently in every known method and this requires time and labor. Moreover, waiting time between drawing blood and plasma separation varies considerably, and coagulation and denaturation of blood therebetween are also a problem. On the other hand, techniques concerning successive drawing blood and plasma separation have been developed from old times, however, plasma separation was carried out by centrifugation.

A device for conducting both drawing blood and plasma separation is disclosed in Japanese Patent KOKAI 52-100783 wherein silica gel is used for plasma separation.

Although various means for obtaining blood plasma directly from blood vessel were developed, none of them has been put to practical use because of troublesome handling, insufficient separation of blood cell components, etc

SUMMARY OF THE INVENTION

An object of the invention is to provide a means capable of collecting a necessary amount of plasma for analysis from blood vessel directly, easily and surely.

The inventors investigated in order to solve the aforementioned problems, and they noted to separate plasma by filtration means because of simple operation. In the case of applying filtration system to a system of conducting drawing blood and plasma separation simultaneously, a great problem is in the development of a blood filtering material which satisfies the conflicting requirements of great blood filtration rate with no occurrence of breakthrough of blood cells and hemolysis. The inventors further investigated, and found that a combination of glass fiber filter and microporous membrane satisfies the requirement. Then, they succeeded in developing a means capable of collecting a necessary amount of plasma for analysis from blood vessel directly by accommodating the blood filtering material in a holder in a state so that the plasma outlet side of the filtering material is apart from the holder. In order to inhibit deposition of fibrins from plasma in the device, it is desirable to add an anticoagulant to at least one place of the device.

Thus, the present invention provides a plasma-collecting device which comprises a blood filtering material comprising glass fiber filter and microporous membrane, a holder having a blood inlet and a plasma outlet accommodating the blood filtering material, a blood-collecting needle being connected to the blood inlet, and a plasma receiver being provided on the plasma outlet side.

Figure 1:
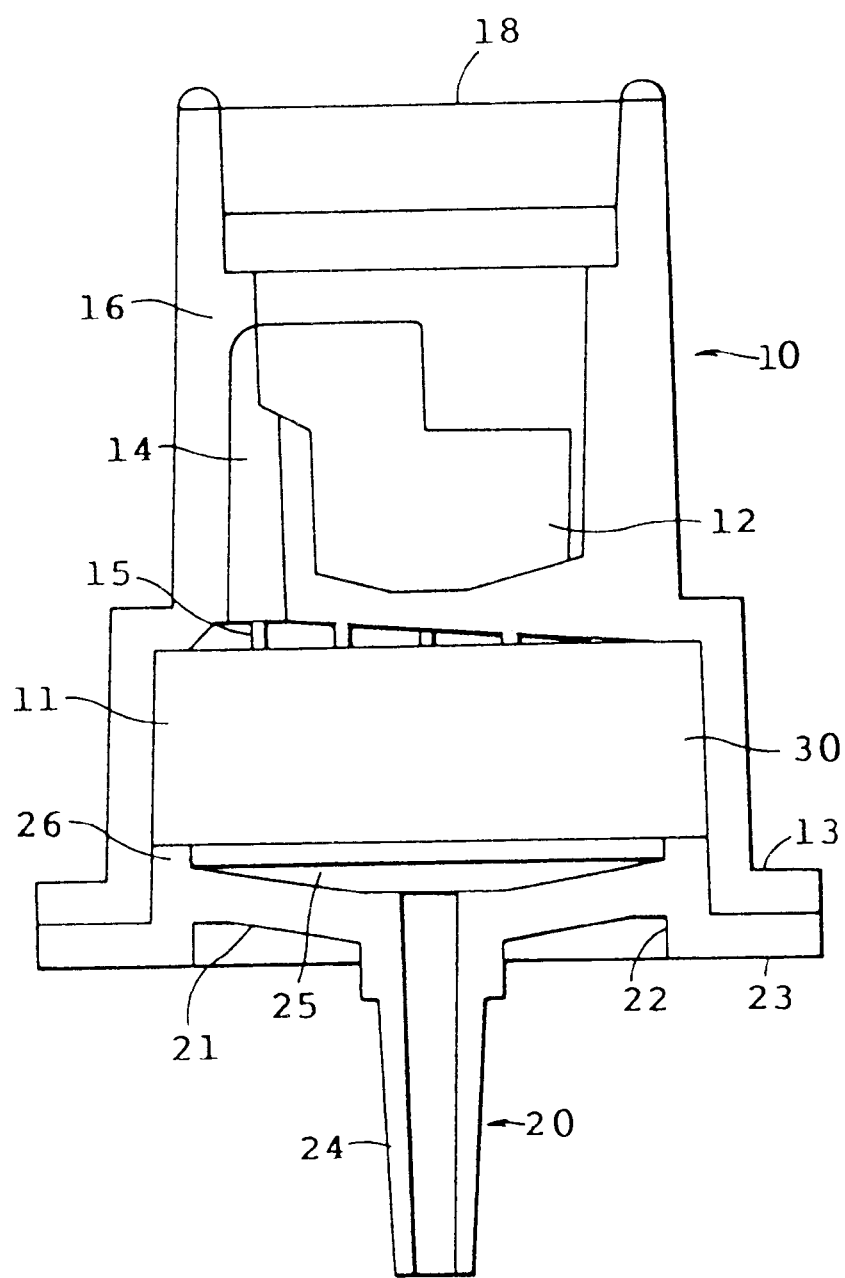
FIG. 1 is a logitudinal section of a blood filter unit applicable to the invention.
Figure 2:
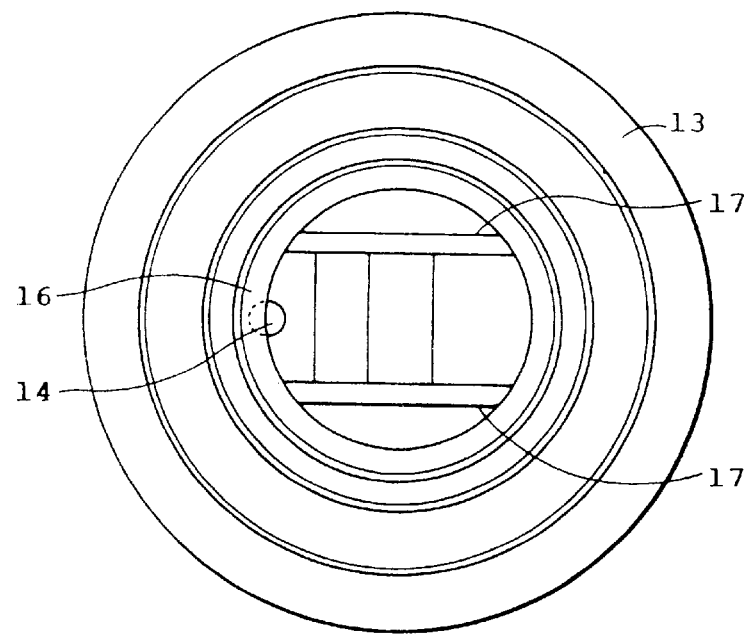
FIG. 2 is a plan view and FIG. 3 is a bottom view of the holder body thereof.

10, 40, 80 . . . Holder body
11, 41 . . . Filter chamber
12, 52, 82 . . . Plasma receiver
13, 23, 43, 53, 71, 72 . . . Flange
14, 54, 83 . . . Plasma passage
15, 55 . . Projection (means for preventing adhesion)
16, 56 . . . Pent-roof
17 . . . Side wall
18, 58 . . . Suction port
20, 50 . . . Cap
21, 42 . . . Circle plate portion
22 . . . Short cylinder portion
24, 44 . . . Blood inlet
25, 45 . . . Space
26, 46 . . . Spacer
27 . . . Rib
30 . . . Blood filtering material
47 . . . Flap
51 . . . Step
57 . . . Partition wall
60, 86 . . . Adapter for suction
61 . . . Suction nozzle
62, 76 . . . Tub 70, 81 ... Blood-collecting needle
73 ... Handle
74, 77 ... Connecting portion
75 ... B Rood passage
84 ... Sealing film
85 ... Hole
87 ... O-ring
88 ... Syringe

DETAILED DESCRIPTION OF THE INVENTION

The blood filtering material used in the invention comprises glass fiber filter and microporous membrane.

Preferable glass fiber filter has a density of about 0.02 to 0.5 g/cm$^3$, preferably about 0.05 to 0.3 g/cm$^3$, more preferably about 0.08 to 0.2 g/cm$^3$, a retainable particle size of about 0.8 to 9 μm preferably 1 to 5 μm. By treating the surface of glass fiber with hydrophilic polymer as disclosed in Japanese Patent KOKAI Nos. 2-208565, 4-208856, filtration proceeds more quickly and smoothly. Lectin, or other reactive reagents to modifiers may be incorporated into glass fiber, or glass fiber may be treated therewith. Two or more glass fiber filters may be laminated.

Microporous membranes having blood cell-separating ability of which the surface has been made hydrophilic separate whole blood into blood cells and plasma specifically without hemolysis to the degree of substantially influencing analytical values. A suitable pore size of the microporous membrane is smaller than the retaining particle size of glass fiber filter, and is 0.2 μm or more preferably about 0.3 to 5 μm, more preferably about 0.5 to 4.5 μm, particularly preferably about 1 to 3 μm. The void content of the microporous membrane is preferably higher, and a suitable void content is about 40 to 95%, preferably about 50 to 95%, more preferably about 70 to 95%. Illustrative of the microporous membranes are, polysulfone membrane, fluorine-containing polymer membrane, cellulose acetate membrane, etc. The surface of the membrane may be hydrolyzed or may be rendered hydrophilic by a hydrophilic polymer or an activating agent.

As the fluorine-containing polymer membrane, there can be the microporous matrix membrane (microporous layer) composed of polytetrafluoroethylene fibrils (fines) disclosed in WO 87/02267, Gore-Tex (W. L. Gore and Associates), Zitex (Norton), Poreflon (Sumitomo Denki), etc. Other fluorine-containing polymer sheets usable as the microporous layer include polytetrafluoroethylene microporous membranes disclosed in U.S. Pat. No. 3,368,872 (Examples 3 and 4), U.S. Pat. No. 3,260,413 (Examples 3 and 4), U.S. Pat. No. 4,201,548, etc., polyvinylidenefluoride microporous membranes disclosed in U.S. Pat. No. 3,649,505 and the like. The microporous membrane of fluorine-containing polymer may be prepared by using a single fluorine-containing polymer or blending two or more kinds of fluorine-containing polymers or further blending one or more polymers not containing fluorine or fibers therewith. As the structure, there are unstretched one, uniaxially stretched one, biaxially stretched one, nonlaminated single layer type, laminated double layer type, such as a membrane laminated to another membrane structure such as a fiber membrane. In the case of nonlaminated type microporous membrane having fibril structure or having been uniaxially or biaxially stretched, microporous membrane having a great void content and a short filtering pass can be prepared by stretching. In microporous membranes having short filtering pass, clogging rarely occurs by solid components (mainly red blood cells) in blood, and the separation time of blood cells and plasma is short. As a result, accuracy in quantitative analysis is improved. The adhesive strength of adhesive used for the partial adhesion to the adjacent microporous membrane can be strengthened by providing the physical activation (preferably glow discharge or corona discharge) disclosed ill U.S. Pat. No. 4,783,315 on at least one side of the microporous membrane of fluorine-containing polymer to render it hydrophilic.

It is well known that fluorine-containing polymer microporous membranes as it is have a low surface tension. As a result, when the membrane is used as the blood cell filtering layer, aqueous liquid samples are repelled and do not diffuse nor permeate over the surface or into the inside. In the invention, the above repelling problem has been resolved by incorporating a sufficient amount of surfactant for rendering the outer surface and the inner space surface of the fluorine-containing polymer microporous; membrane substantially hydrophilic thereinto. In order to impart a hydrophilic property sufficient for diffusing, permeating or moving an aqueous liquid sample over the surface or into the inside of the fluorine-containing polymer microporous membrane without repelling to the membrane, in general, it is necessary that the space surface of the membrane is coated with a surfactant in an amount of about 0.01 to 10%, preferably about 0.1 to 5%, more preferably about 0.1 to 1% of the void volume of the membrane. For example, in the case of a fluorine-containing polymer microporous membrane 50 μm in thickness, a preferred amount of surfactant to be impregnated is usually in the range of 0.05 to 2.5 g/m$^2$. As the method of impregnating surfactant into a fluorine-containing microporous membrane, a common method comprises immersing the fluorine-containinng microporous membrane in the surfactant solution dissolved in a low boiling point (a preferable boiling point is in the range of about 50° C. to about 120° C.) organic solvent (e.g. alcohols, esters, ketones) to permeate into the inner spaces of the membrane substantially sufficiently, taking the membrane out of the solution slowly, and then drying by blowing air (preferably warm air).

As the surfactant for rendering the fluorine-containing polymer microporous membrane hydrophilic, the surfactant may be nonionic, anionic, cationic or ampholytic. However, nonionic surfactants are advantageous for the multilayer analytical elements for analyzing whole blood samples, because nonionic surfactants have a relatively low hemolytic activity among the above surfactants. Suitable nonionic surfactants include alkylphenoxypolyethoxyethanol, alkylpolyether alcohol, polyethyleneglycol monoester, polyethyleneglycol diester, higher alcohol-ethylene oxide adduct (condensate), polyol ester-ethylene oxide adduct (condensate). higher fatty acid alkanol amide, etc. Examples of the nonionic surfactant are as follows: As the alkylphenoxypolyethoxyethanol, there are isooctylphenoxypolyethoxyethanols (Triton X-100; containing 9–10 hydroxyethylene units on average, Triton X-45; containing 5 hydroxyethylene units on average) and nonylphenoxypolyethoxyethanols (IGEPAL CO-630; containing 9 hydroxyethylene units on average, IGEPAL CO-710; containing 10–11 hydroxyethylene units on average, LENEX 698; containing 9 hydroxyethylene units on average). As the alkylpolyether alcohol, there are higher alcohol polyoxyethylene ethers (Triton X-67; CA Registry No. 59030-15-8), etc.

The fluorine-containing polymer microporous membrane may be rendered hydrophilic by providing one or more water-insolubilized water-soluble polymers in its porous spaces The water-soluble polymers include oxygen-containing hydro carbons, such as polyacrylamide, polyvinylpyrrolidone, polyvinylamine and polyethylenamine, negative charge-containing ones such as polyvinyl alcohol, polyethylene oxide, polyethylene glycol, methyl cellulose, ethyl cellulose, hydroxyethyl cellulose and hydroxypropyl cellulose, nitrogen-containing ones, such as polyacrylic acid, polymetacrylic acid and polystyrene sulfonic acid, and the like. The water-insolubilization may be conducted by heat treatment, acetal-inducing treatment, esterification, chemical reaction by potassium dichromate, crosslinking by ionizable radiation, or the like. Details are disclosed in Japanese Patent KOKOKU Nos. 56-2094 and 56-16187.

The polysulfone microporous membrane can be prepared by dissolving polysulfone into dioxane, tetrahydrofuran, dimethylformamide, dimethylacetamide. N-methyl-2-pyrolidone or a mixed solvent thereof to obtain a raw liquid for forming film, casting into film by flowing directly into a coagulating solution, washing, and then drying. Details are disclosed in Japanese Patent KOKAI No. 62-27006. In addition, polysulfone microporous membranes are also disclosed in Japanese Patent KOKAI Nos. 56-12640, 56-86941, 56-154051, etc., and they are applicable to the invention. The polysulfone microporous membrane can be rendered hydrophilic, similar to the fluorine-containing polymer, by incorporating surfactant or providing water-insolubilized water-soluble polymer.

As the other nonfibrous microporous membranes, blushed. polymer membranes composed of a cellulose ester, such as cellulose acetate, cellulose acetate/butyrate or cellulose nitrate, disclosed in U.S. Pat. No. 3,992,158 is preferable. Microporous membranes of polyamide, such as 6-nylon or 6,6-nylon, or polyethylene, polypropylene, or the like are also usable. Other nonfibrous microporous membranes usable include continuous microspace-containing porous membranes where polymer particulates, glass particulates, diatomaceous earth or the like are joined by a hydrophilic or non-water-adsorptive polymer, such as disclosed in U.S. Pat. No. 3 992 158, and U.S. Pat. No. 4 258 001.

Suitable effective pore size of the nonfibrous microporous membrane is 0.2 to 10 μm, preferably 0.3 to 5 μm, particularly preferably 0.5 to 5 μm. The effective pore size of the nonfibrous porous membrane in the invention is the pore size measured by the bubble point method according to ASTM F316-70. In the case that the nonfibrous porous membrane in a membrane filter is composed of blushed polymer prepared by the phase separation method, the liquid passages in the thickness direction are, in general, the narrowest at the free surface (glossy face) in the manufacturing process of the membrane, and the pore size in section of each liquid passage stipulated as a circle is the smallest near the free surface. The minimum pore size of passages in the thickness direction per unit area has a distribution in facial direction of the membrane filter, and the maximum value determines filtration performance. In general, it is determined by the limit bubble point method.

As mentioned above, in the membrane filter composed of blushed polymer prepared by the phase separation method, liquid passages in the thickness direction become the narrowest at the free surface (glossy face) in the manufacturing process of the membrane. In the case of using the membrane as the nonfibrous porous membrane of the filtering material of the invention, it is preferable to face the glossy face of the membrane filter toward the side to discharge the plasma portion.

A third filtering material may be incorporated into this blood filtering material. The third filtering material may be filter paper, nonwoven fabric, woven fabric such as plain weave fabric, knitted fabric such as tricot fabric, etc. Among them, woven fabric and knitted fabric are preferred. The woven fabric or the like may be treated by, glow discharge as disclosed in Japanese Patent KOKAI No. 57-66359. The third filtering material is preferably interposed between the glass fiber filter and the microporous membrane.

Preferable microporous membranes are polysulfone membrane, cellulose acetate membrane and the like, and particularly preferred is polysulfone membrane. In the blood filtering material of the invention, the glass fiber filter is located on the blood inlet side and the microporous membrane in located on the filtrate outlet side. The most preferable blood filtering material is a laminate of the glass fiber filter and polysulfone membrane laminated in this order from the blood inlet side.

In the plasma-collecting device of the invention, the glass fiber filter and polysulfone microporous membrane, etc. may be superimposed and put in a holder. However, respective layers may be integrated by joining each other using partially disposed (e.g. spot) adhesive, according to disclosures in Japanese Patent KOKAI Nos. 62-138756-8, 2-105043, 3-16651, etc.

In the filtering material of the invention, it is thought that the filter material does not trap blood cells only by the surface, but catches to remove blood cells gradually by entangling at first large blood cell components and then smaller blood cell components in the space structure with permeating in the thickness direction in total of the filtering material, called the volumetric filtration.

The quantity of whole blood filterable by this system is greatly influenced by the void volume existing in glass fiber filter and the volume of blood cells in the whole blood. When the density of the glass fiber filter is high (pore size to retain particles is small), erythrocytes are trapped in the vicinity of glass fiber filter surface, voids in the glass fiber filter are clogged in a very thin region from the surface, and accordingly, filtration does not proceed thereafter. As a result, recovered plasma volume by filtration is small. On that occasion, when this filter material is sucked by stronger suction in order to increase recovered plasma volume, blood cells are destroyed, i.e. hemolyzed. That is, the filtration becomes similar to surface filtration, and utilization rate of void volume of the filter is low.

As an indicator corresponding to void volume or filtrate volume of plasma, water permeation speed is suitable. The water permeation speed is determined by putting a glass fiber filter with a definite area in a closed filter unit of which the inlet and outlet can be connected by a tube, adding a definite volume of water, and pressurizing or sucking at a constant pressure. The water permeation speed is filtrate volume per unite area and time, and expressed by ml/sec.

For example, glass fiber filter 20 mm φ in diameter is put in a filter unit, and a 100 ml syringe containing 60 ml water is connected to the top of the filter unit. Water flows down naturally, and volume of water passing through the glass filter from 10 sec to 40 sec after starting is measured as the water permeation volume, and the water permeation speed per unit area is calculated from it.

Glass fiber filters particularly suitable for plasma separation have a water permeation speed of about 1.0 to 1.3 ml/sec, and illustrative of the glass fiber filters are Whatman GF/D, Toyo Roshi GA-100, GA-200 and the like. Furthermore, the glass fiber filter can be prepared by suspending glass fibers of a commercial glass fiber filter in hot water, and then making the glass fibers into a low density sheet (density: about 0.03 g/cm$^3$) on a nylon net. The glass fiber filter thus prepared shows good plasma separating ability.

A suitable thickness of the glass fiber filter varies according to the plasma volume to be recovered and density (void content) and area of the glass fiber filter. A necessary amount of plasma for analyzing plural items using dry analytical elements is 100 to 500 μl. In practical viewpoint, a glass fiber filter having a density of about 0.02 to 0.2 g/cm$^3$ and an area of 1 to 5 cm$^2$ is suitable. In this case, a suitable thickness of the glass fiber filter is about 1 to 10 mm, preferably about 2 to 8 mm, more preferably about 4 to 6 mm. The above thickness can be made by superimposing 1 to 10 sheets, preferably 2 to 6 sheets of glass fiber filter.

A suitable thickness of the microporous membrane is about 0.05 to 0.5 mm, preferably about 0.1 to 0.2 mm, and the number of microporous membranes is usually one. However, two or more sheets of microporous membrane may be used, if necessary.

The holder accommodates the blood filtering material, and is provided with a blood inlet and a plasma outlet. The holder is, in general, formed of a body accommodating the blood filtering material and a cap, and every one is provided with at least two apertures. One is used as the blood inlet, and the other is used as the plasma outlet, optionally further as a suction port. A suction port may be provided separately. In the case that the holder is rectangular and is provided with the cap on a side of the holder, both of the blood inlet and the plasma outlet may be provided on the holder body.

The volume of the filter chamber which accommodates the blood filtering material is necessary to be greater than the total volume of the blood filtering material both in a dry state and in a swelled state upon absorbing a sample (whole blood). When the volume of the filter chamber is smaller than the total volume of the blood filtering material, filtration does not proceed efficiently and hemolysis occurs. A suitable ratio of the volume of the filter chamber to the total volume of the blood filtering material in a dry state is, in general, 101 to 200%, preferably 110 to 150%, more preferably 120 to 140%, although the ratio varies according to the swelling degree of the filtering material.

Besides, it is necessary that the periphery of the blood filtering material is closely fitted to the wall of the filter chamber so as not to form a bypass of whole blood without passing the filtering material.

In an aspect of the plasma-collecting device of the invention, a means for preventing adhesion of the blood filtering material on the plasma outlet side is provided. The means is to separate the blood filtering material from the plasma outlet side of the holder so as to proceed filtration in broader area, preferably over all face of the blood filtering material. Such a means includes to render the filtrate outlet side of the holder concave, such as in cone or partial sphere, to provide a solid material arranged so as to leave liquid passages, such as plural projections, about 1 to 100 projections, preferably 1 to 5 projections, per 1 cm$^2$ on the filtrate outlet side of the holder, a spacer, such as net, grains or ring(s), and the like. In the case of forming concave, the filtrate outlet is preferably provided on the deepest position.

Figure 7:
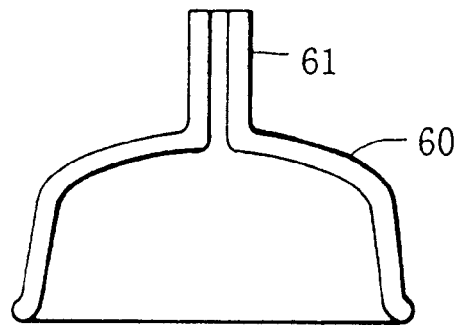
FIG. 7 is a longitudinal section of an adapter which is attached to the blood filter unit of FIG. 1.

The following 4 holders were prepared. (1) The blood filtering material was in contact with the filtrate outlet side, and the filtrate outlet was provided at the center of the filtrate outlet side, or (2) the filtrate outlet was provided in the vicinity of the periphery of the filtrate outlet side. (3) A step-formed concave (1 mm in depth) was formed as shown in FIG. 7, and the filtrate outlet was provided at the center, or (4) the filtrate outlet was provided in the vicinity of the periphery. Using the above holders, recovered volume of plasma was measured and found to be a (1) 50 μl, (2) r40 μl, (3) 243 μl and (4) 330 μl.

The shape of the projections may be column, square column, cone and truncations thereof, pyramid and thereof, mushroom, irregular form, or any other form, but the top of the projections is preferably flattened or rounded.

A suitable total contact area of the solid material arranged so as to leave liquid passages, such as the top of the projections with the blood filtering material upon filtering is about 1 to 50%, preferably about 5 to 20% of the surface area of the blood filtering material of effective filtering area, i.e. except periphery for holding the blood filtering material. Since the amount of the blood filtered by the blood filter unit of the invention is small, a suitable space left by the means for preventing adhesion upon filtering blood is about 10 to 500 μl. preferably about 50 to 200 μl. The filtrate outlet side of the holder is preferably formed in a funnel shape so as to facilitate discharge of plasma which is filtrate.

A plasma receiver which receives the plasma is provided, on the plasma outlet side of the holder. The plasma receiver may be provided in the holder, or as a separate body connected to the holder by a tube. When an analyzer is equipped with a plasma receiver, it can be used. In the viewpoint of designing an analyzer which analyzes the plasma obtained by the plasma-collecting device of the invention, it is preferable to suck the plasma by the analyzer at the center of the holder, and as a result, a passage of plasma to the plasma receiver is formed excepting the center. When the passage is formed in the vicinity of the periphery of the plasma reciever, molding is facilitated. Moreover, troubles of entering plasma into a suction duct can be prevented which tends to occur in the case of low viscosity plasma. Since it is possible to spout plasma from the plasma passage by suction in the case of a small hematocrit value blood, a baffle, such as a pent-roof, is preferably provided at the exit of the passage. The bottom of the plasma receiver is preferably inclined, such as in a form of reversed cone so as to facilitate the suction by a suction nozzle of an analyzer. Moreover, since recovered volume of plasma considerably varies according to hematocrit value, it is preferable to provide an over flow structure. The capacity of the plasma receiver may be about 10 μm to 2 ml.

In order to examine effects of the space formed on the blood inlet side of the holder, the following experiments were carried out.

Shape of Inlet Side of Holder and Recovery of Plasma (1) The following three structures wherein blood was supplied from the underside were examined:

(1) The bottom is flat, and sucked blood immediately contacts glass fiber filter.

(2) The bottom is in a funnel shape, and sucked blood is spread to an area in a certain degree and then contacts glass fiber filter.

(3) A spacer (1 mm in thickness) is interposed between the bottom and glass fiber filter, and sucked blood is first accumulated under the bottom. By further sucking, the level of blood elevates, and blood contacts over all the area of glass fiber filter almost simultaneously.

(2) Blood-Drawing

Vein blood was drawn from a healthy woman using a 10 ml vacuum blood-drawing tube containng heparin (Terumo) .and 2 ml was pipetted into each sample tube made of plastic. Hct value was 41%.

(3) Assembling of Filter Unit

Six sheets of glass fiber filter (GF/D, Whatman) punched into disc 19.7 mm φ in diameter were put in a filter holder as shown in FIG. 1 (except the upper structure of the body), and a polysulfone membrane (Fuji Photo Film Co., Ltd.) was superposed thereon. A joint for sucking air was attached further thereon, and connected to a small size peristaltic pump.

(4) Filtration of Blood

A silicone tube 4 cm in length was connected to the blood inlet of the filter unit assembled in the above (3), and the end of the tube was inserted into the sample tube containing a blood sample prepared in the above (2), and fixed in almost vertical direction.

The suction speed of the peristaltic pump was set at 2.8 ml/sec, and suction was conducted twice each for 10 seconds. The interval between the first suction and the second suction was 1 second. Plasma was separated and accumulated in the plasma receiver.

(5) Results

In ①, obtained plasma volume was very small, and the degree of hemolysis was great, and an the other hand, in ③, a great volume of plasma with good quality was recovered. In ②, plasma obtained was intermediate between ① and ③, and recovered volume of the plasma was insufficient.

As mentioned above, it is preferable to provide a space also on the blood inlet side so that filtration proceeds over all face of the blood filtering material. Thereby, first, air is sucked over the entire inlet face of the blood filtering material, and as a result, blood is sucked and filtered with spreading over the entire inlet face. Since the blood filtering member on the blood inlet side acts in, the direction to move apart from the blood inlet race of the holder upon filtering, the space can be formed by a spacer, such as a ring rib or several projections, for holding the blood filtering material at the periphery on the inner wall of the holder. It is also possible to project the periphery of the cap toward the blood filtering material side, and the projection is functioned as the spacer. A suitable volume of the space between the blood filtering material and the blood inlet face of the holder is about 10 to 500 μl, preferably about 50 to 200 μl upon filtering.

The filter unit of the invention is made into a closed structure except the blood inlet and the plasma outlet by attaching a cap to the holder body.

As the material of the holder, thermoplastic or thermosetting plastics are preferable. Illustrative of the plastics are general-purpose polystyrene, high impact polystyrene, methacrylate resin, polyethylene, polypropylene, polyester, nylon, polycarbonate, etc. The material may be transparent or opaque.

Fitting of the cap to the holder body may be any means, such as adhesion using adhesive or fusion welding. On that occasion, either periphery of the holder body or of the cap is located on the inside, or both peripheries are butted. The fitting may be in a state of detachable utilizing screws or the like.

The shape of the blood filtering material is not restricted, but disc and polygon is preferable in view of production. By rendering the size of the blood filtering material slightly greater than the inside section of the holder body (i.e. filter chamber), breakthrough of blood at the periphery of the filtering material can be prevented. To render the shape square is preferable because of no generation of cutting loss.

The blood-collecting needle is connected to the blood inlet of the holder. The blood-collecting needle is inserted into blood vessel, and a needle for injection can be used as it is, or after processing its connecting portion. The blood-collecting needle may be connected to the holder directly or through a tube., etc. It is necessary that the blood-collecting needle is stored in a germfree state, and therefore, the needle may be attached immediately before the use.

The anticoagulant inhibits blood coagulation caused by deposition of fiblin from blood, and exemplary anticoagulants are a salt, such as ammonium, sodium, lithium or potassium of heparin, plasmin, EDTA, sodium oxalate, sodium citrate, etc. Heparin is perticularly preferable because of having a high ability to inhibit deposition of fiblin. The amount to be used of the anticoagulant is necessary for inhibiting coagulation or recovered plasma, and accordingly, depends on the volume of recovering plasma. In general, a suitable amount of the anticoagulant is about 0.1 to 100 unit, preferably 0.5 to 60 unit.

The anticoagulant is disposed at least one place in a passage from the blood-collecting needle to the plasma receiver The anticoagulant may be located at any part of the blood passage. However, in order to decrease the influence on liquid flow, it is preferable to incorporate the anticoagulant into the blood filtering material or plasma receiver. A special tank for the anticoagulant may be newly incorporated. The anticoagulant is preferably in a dry state so as not to deteriorate during storage. The anticoagulant is in a state capable of contacting blood or plasma upon filtering and dissolving thereinto. For example, in the case of the blood filtering material, the anticoagulant is impregnated in one or more layers followed by drying. In the case of putting in a plasma receiver, one drop of an aqueous solution of anticoagulant, such as heparin, is dropped in the plasma receiver and then dried. In order to prevent flying away of the dried matter of the anticoagulant, the antiocoagulant may be wrapped by a film of water-soluble polymer, such as PVA or PVP, or impregnated into fibers or the like and then dried. The wrapped matter or impregnated matter is put in or fixed to the plasma receiver.

Upon using the plasma-collecting device of the invention, the blood-collecting needle is inserted into vein or artery in an arm or another position, and plasma which is the filtrate discharged from the plasma outlet is received by the plasma receiver. In general, suction from the plasma outlet side is needed for filtration, and a suction device, such as syringe, vacuum blood-collecting tube or suction pump, may serve as the suction means therefor. A suitable suction speed is 0.1 to 100 ml/min. preferably 1 to 70 ml/min, more preferable 5 to 50 ml/min. In the case of collecting blood from artery, the suction means is usually not necessary. The plasma-collecting device is, in general, disposable.

When blood is collected from arm or another position using the plasma-collecting device of the invention, the plasma-collecting device tends to be held in a horizontal or inclined state rather than in a vertical state. As a result, it is possible that the blood inlet is situated above the plasma outlet, and there is a fear of collected plasma streaming into the suction device employed. Thereupon, it is preferable to attach a sealing member to the upper opening of the plasma receiver in order to avoid such a trouble. It is necessary that the sealing member is provided with an air passage, such as a hole (which may be a slit, notch, etc.) in order to ensure air flow through suction filtration. The air passage is necessary to be provided at a position where the discharged plasma upon drawing blood does not close the passage nor enter into the suction device. The sealing member also functions to prevent evaporation while storing the collected plasma. In order to exhibit the above functions sufficiently, it is preferable that the air passage has a minimum size capable ensuring air flow upon suction.

The air passage itself may be the entrance of a device which sucks the plasma in the plasma receiver upon measurement, such as a plastic pipette or a sampling nozzle incorporated in an automatic analyzer. The entrance may be formed upon suction separate from the passage, and in this case, it is preferable that the sealing member is made of a material capable of being pierced easily by the top of the device which sucks the plasma.

The sealing member upon collecting plasma may be different from the sealing member upon sucking the plasma for measurement. For example, the sealing member upon collecting plasma has a structure detached together with the adapter for suction after blood filtration is finished, and thereafter, the plasma receiver is sealed again by attaching a new sealing member. In the case of conducting blood filtration and measurement successively, for example, in an urgent inspection, it is enough to consider the prevention against evaporation after collecting plasma. In such a case, this form of sealing is preferable.

The sealing member may cover the opening of the plasma receiver entirely before serving. In this case, it is preferable that the sealing member is a film of which a part can be easily peeled off or which can be pierced with a top of a needle or pipette.

As the material of the sealing member, plastic films are most suitable, but other materials capable of exhibiting the aforementioned functions may be used, such as metal film, paper and cloth. Molded plastic caps are also usable. The surface is preferably rendered water repellent. Illustrative of the films are "Parafilm" (American National Co.), "Sealon" (Fuji Photo Film Co., Ltd.), polyvinylidene chloride films ("Saran Wrap", Asahi Chemical Ind. Co., Ltd., etc.), vinylidene chloride-based films ("Kure Wrap", Kureha Chemical Ind. Co., Ltd., etc.), polyethylene films and so on.

A suitable film thickness of the sealing member is about 50 $\mu$m to 2 mm, preferably 100 $\mu$m to 1 mm, more preferably 150 to 750 $\mu$m.

EXAMPLES

Example 1

A blood filter unit illustrated in FIGS. 1–6 was prepared. The filter unit was composed of a holder body 10 and a cap 20, as shown in FIG. 1 which illustrates an assembled state of the filter unit.

Figure 3:
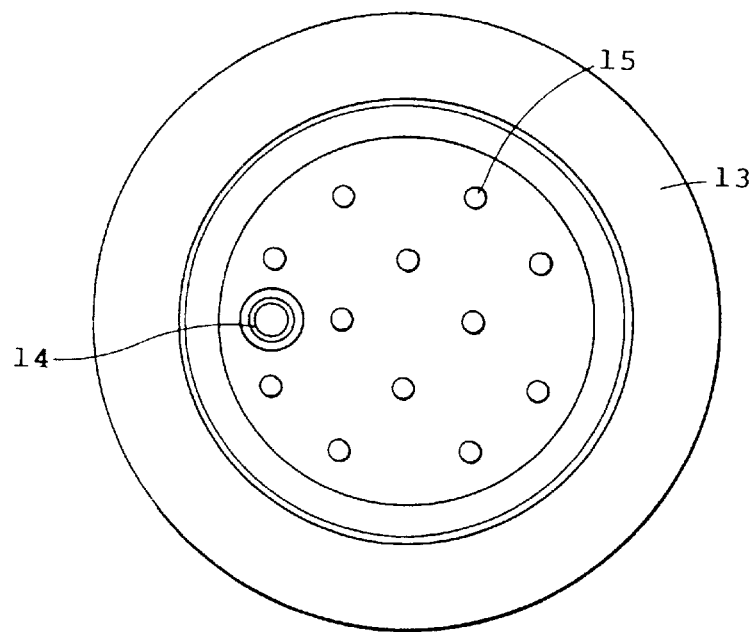
Figure 4:
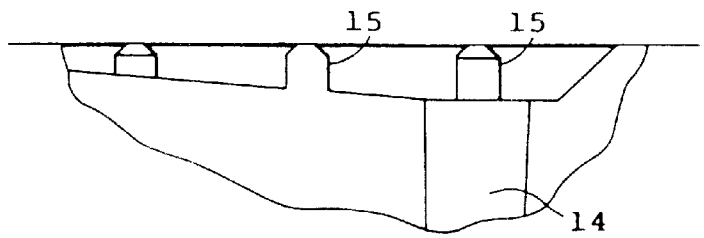
FIG. 4 is an enlarged partial section indicating the shape of projections.
Figure 5:
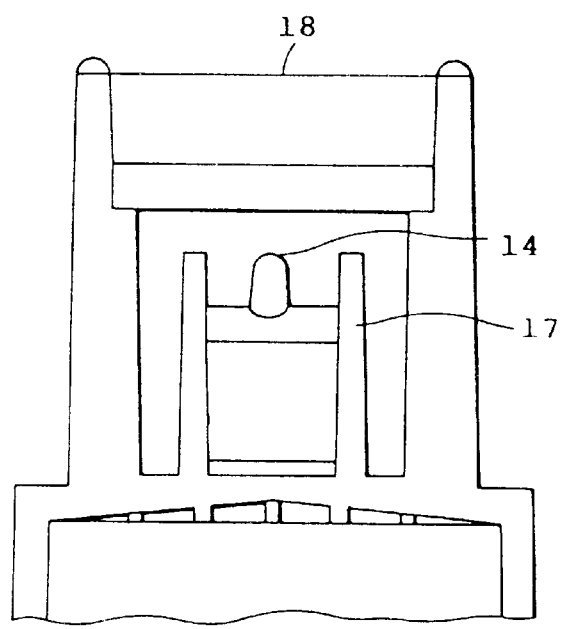
FIG. 5 is a longitudinal section of an upper part of the holder body cut in the direction rectangular to FIG. 1 seen toward a plasma passage.
Figure 6:
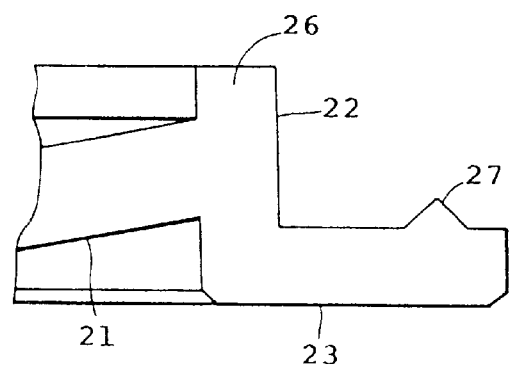
FIG. 6 is an enlarged partial section indicating a flange portion of a cap.

The holder body 10 is cylindrical consisting of a small diameter portion and a large diameter portion connected thereto. The upper portion is composed of a plasma receiver 12 and a connecting portion to suction side, and the lower portion becomes a filter chamber 11 for accommodating blood filtering material(s) 30. The size of the filter chamber 11 is 19.5 mm in inside diameter and 10 mm in depth. Since the upper part of the cap 20 enters there up to 3 mm in height, the height of the filter chamber becomes 7 mm. A flange 13 for connecting the cap is formed outward on the outside of the lower end of the holder body 10. The entrance of plasma passage 14 is provided at the ceiling of the filter chamber 11 near the left end in FIG. 1, and the ceiling is formed into a thin funnel shape wherein the entrance is provided on the top position. The height between the periphery and the entrance is 1 mm. As shown in FIG. 3, 12 projections 15 are formed on the ceiling at almost the same interval. Each projection 15 is a short rod, and the lower end is cut so as to position in the same plane. Periphery of the end of each projection 15 is cut off.

A pent-roof 16 is provided at the exit of plasma passage 14, and the underside of the pent-roof 16 is formed in an arc-shaped to prevent spouting upward of discharged plasma. A plasma receiver 12 is formed by partitioning the cylindrical holder body 1 by two side walls 17 in parallel interposing the exit of the plasma passage so as to obtain a sufficient depth even in a small plasma volume. The upper, end of the holder body is opened, and it becomes a suction port 18 when connected to a suction means. The upper end (suction port 18) of the holder body is rounded in order to ensure liquid-tight ability after connecting to the suction means.

A cap 20 is composed of circle plate portion 21 in a thin funnel shape located at center, short cylinder portion 22 formed surrounding the periphery of the circle plate portion 21, a flange 23 formed outward on the outside of the lower end of the short cylinder portion 22, and a nozzle-shaped blood inlet 24 extended downward from the center of the circle plate portion 21. The diameter of the circle plate portion is 17 mm, the depth in the funnel portion is 1 mm, the height of the short cylinder portion 22 is 4.5 mm, and the outer diameter of the flange 23 is 28 mm. The connecting position of the circle plate portion 21 to the short cylinder portion 22 is made lower than the upper edge of the short cylinder portion 22 by 1 mm, and thereby, the upper end functions as a spacer 26 for separating the underside of the blood filtering material 30 from the top face of the funnel-shaped circle plate portion 21 to form a space 25. On the top face of flange 23 facing the flange 13 of the holder body 10, a rib 27 is formed in ring shape.

The rib 27 collects ultrasonic energy upon fusion bonding the flanges 13, 23 by ultrasonic wave to ensure liquid-tight ability at the joined portion.

A polysulfone microporous membrane (Fuji Photo Film Co., Ltd.) was put in the filter chamber 11, and then, six sheets of glass fiber filter (Whatman GF/D) punched into disc 19.7 mm in diameter were further put in the filter chamber 11 with pressing by a force of about 80 g. Respective filter layers with contact with each other lightly. Then, the cap 20 was fitted, and joined by ultrasonic welding.

Thus, a blood filter unit was completed.

Figure 8:
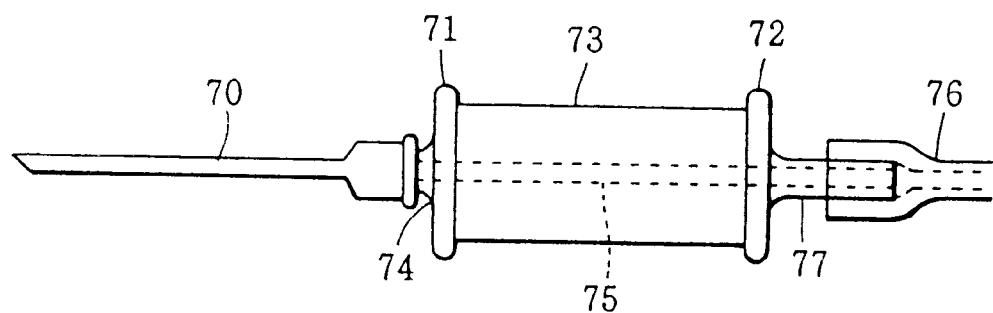
FIG. 8 is a side view of a blood-collecting needle.

5 $\mu$l (0.1 unit) heparin was put in the plasma receiver 12 of the blood filter unit, and an adapter for suction 60 shown in FIG. 7 was attached to the suciton port 18, and a blood-collecting needle 70 shown in FIG. 8 was attached to the blood inlet 24, respectively. The adapter 60 was made of flexible polyethylene, and a tube 62 is connected to the suction nozzle 61 located at the center of the adapter 60. A suction means, such as syringe (not illustrated), was connected to the other end of the tube 62.

Figure 10:
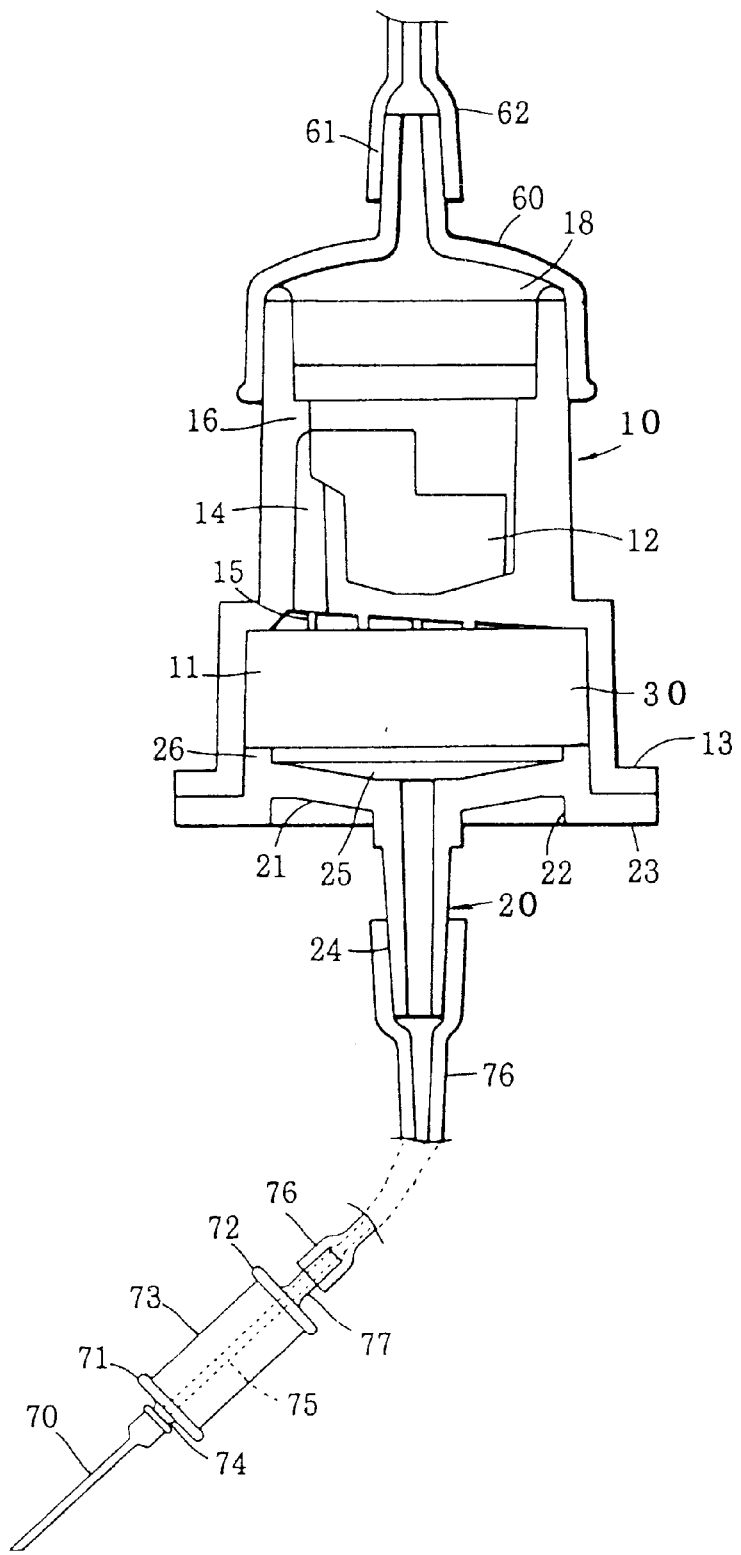
FIG. 10 is a longitudinal section of a plasma-collecting device embodying the invention.

The blood-collecting needle was fitted to a connecting portion 74 projected from the front end of a short columnar handle 73 of which at both ends flanges 71, 72 were formed. A blood passage 75 penetrated the handle 73 from the front end to the rear end at the axis thereof. A connecting portion 77 for fitting a tube 76 was projected from the rear end of the handle 73. The other end of the tube 76 was connected to the blood filter unit by fitting to the blood inlet 24. The plasma-collecting device thus completed was shown in FIG. 10.

Example 2

Figure 11:
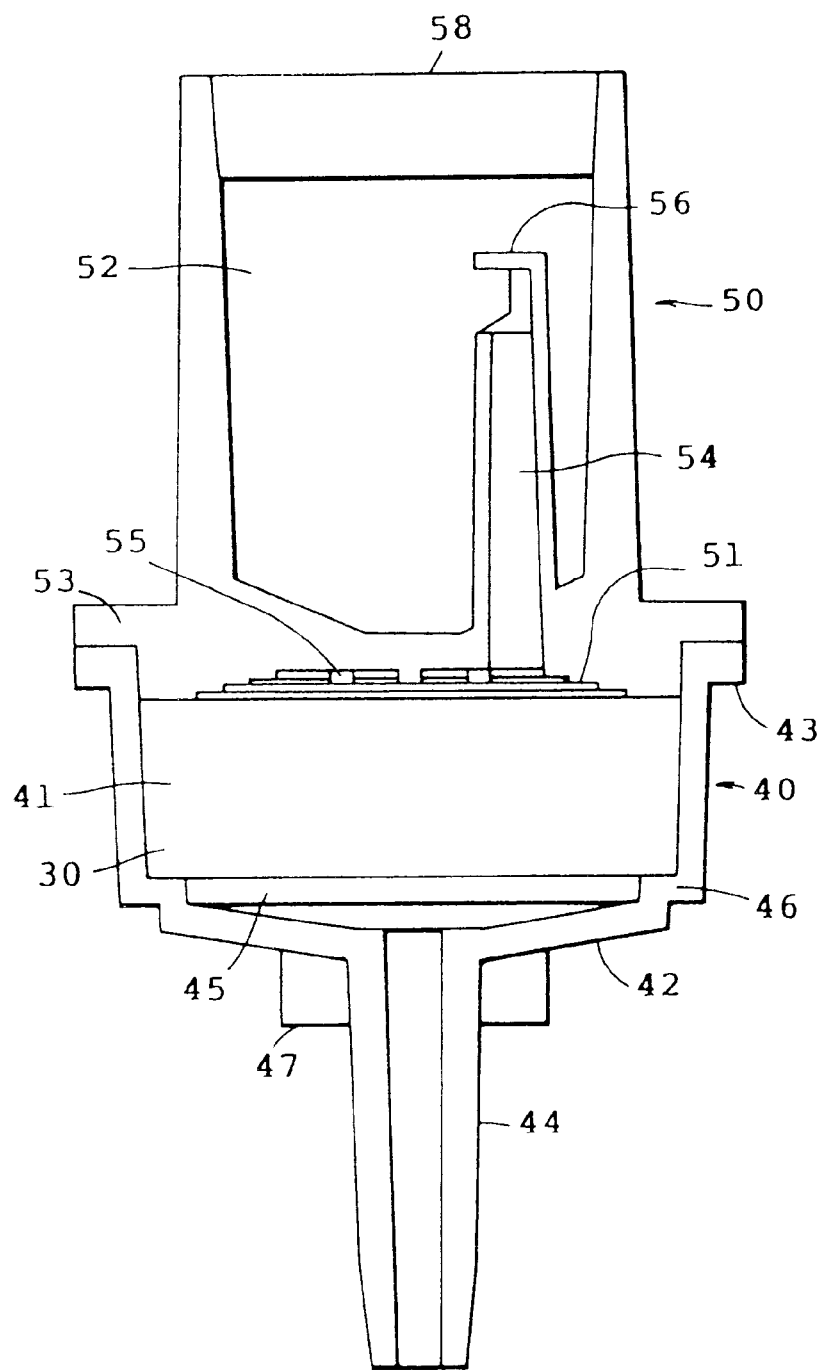
FIG. 11 is a longitudinal section of another blood filter unit also applicable to the inveniton.
Figure 12:
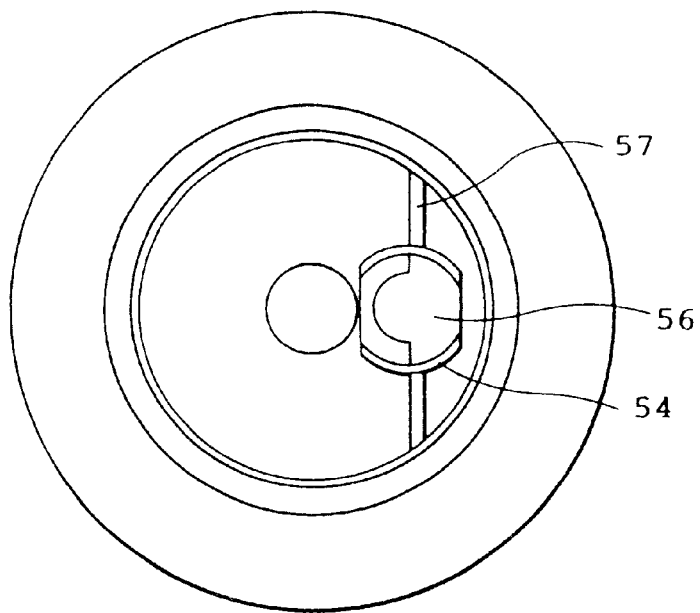
FIG. 12 is a plan view and FIG. 13 is a bottom view thereof.
Figure 13:
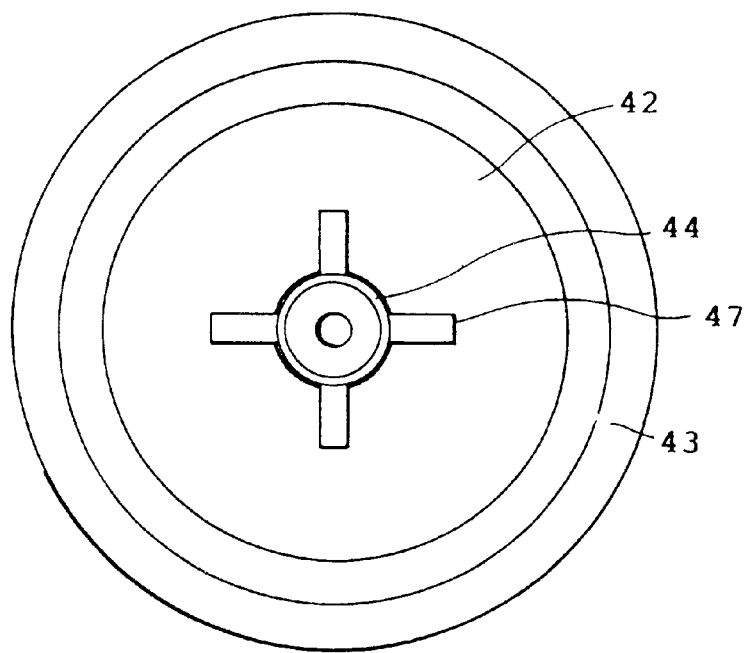

A blood filter unit illustrated in FIGS. 11–13 was prepared. The filter unit was composed of a holder body 40 and a cap 50, as shown in FIG. 11 which illustrates an assembled state of the filter unit.

The holder body 40 is formed of a filter chamber 41 for accommodating blood filtering material(s) 30 and a flange 43 formed outward at the upper end of the filter chamber 41.

The bottom of the filter chamber 41 is made by a thin funnel-shaped circle plate portion 42 with a step portion near the periphery, and a nozzle-shaped blood inlet 44 is extended downward from the center of the circle plate portion 42. The above step portion functions as a spacer 46 for separating the underside of the blood filtering material 30 from the funnel-shaped circle plate portion 42 to form a space 45.

The underside of the bottom of the cap 50 is recessed to form an upper space wherein 4 steps 51 are formed in concentric circle shape. Five projections 55 are projected downward as the means for preventing adhesion on the central portion in the shape of 5 spots is die. A plasma passage 54 in a smokestack-shaped and stands upward from near the middle point between the center and periphery, and a pent-roof 56 which prevent spouting upward of discharged plasma is provided at the top of the plasma passage 54 in the horizontal direction. As shown in FIG. 12, the pent-roof 56 has a shape of a combination of two half circles. The half circle on the periphery side is consistent with the outer wall of the plasma passage 54, and the half circle on the center side is consistent with extension of the inner wall of the plasma passage 54. A partition wall 57 is formed straight interposing the plasma passage in order to ensure a sufficient depth even in a small plasma volume. The upper end of the plasma receiver 52 is opened, and it becomes a suction port 58. A flange 53 is formed outward near the lower end of the cap 50, and the flange 53 is joined to the flange 43 of the holder body by ultrasonic welding. A rib (not illustrated) is formed on the face of the flange 53 facing the flange 43 of the holder body so as to ensure liquid-tight ability at the joined portion.

50 μl of 1000 U/ml heparin lithium aqueous solution was sucked by a micropipette, and dropped onto the handle 73 connected to the blood inlet 44, and then dried by leaving it.

Example 3

Figure 9:
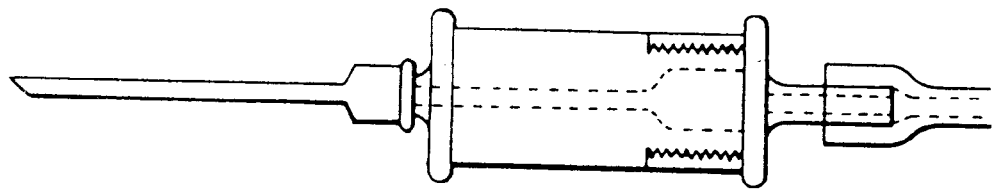
FIG. 9 is a side view of another blood-collecting needle.
Figure 14:
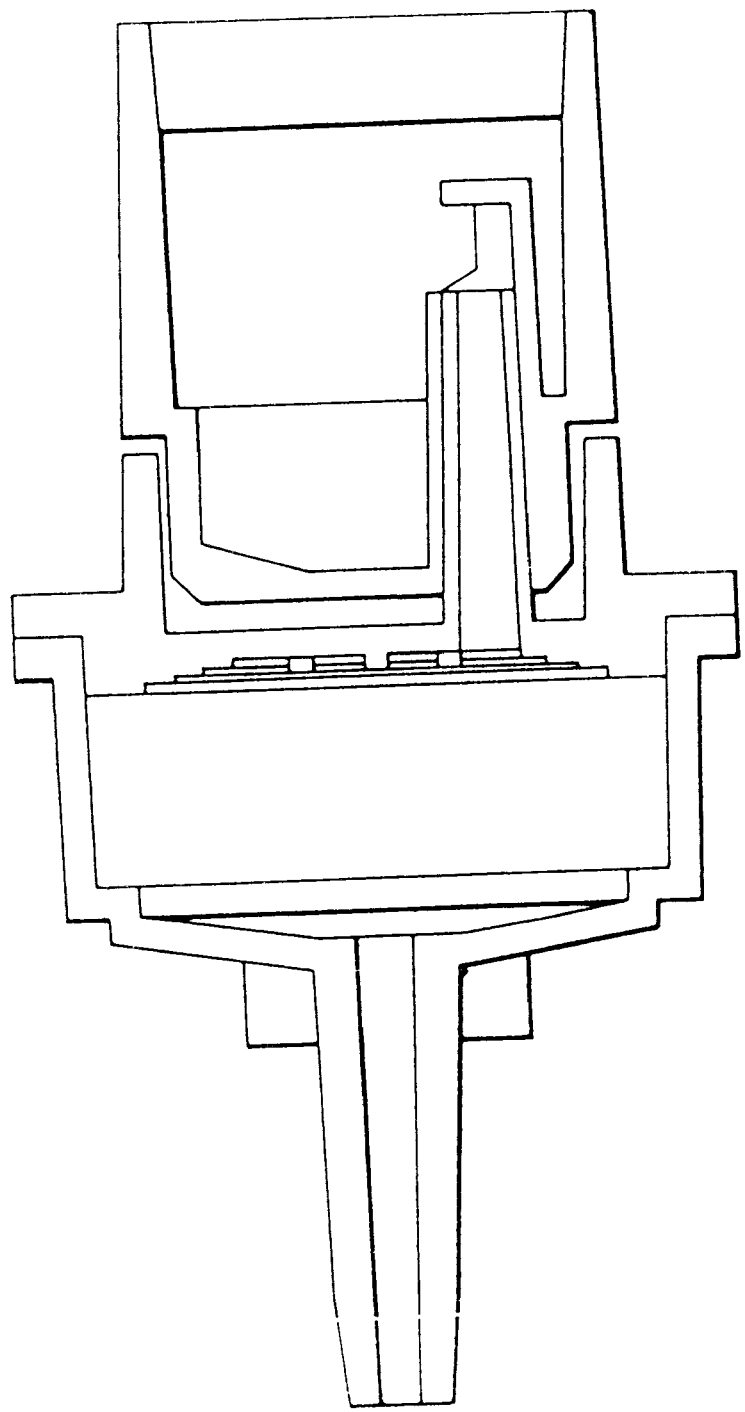
FIG. 14 is a longitudinal section of another blood filter unit applicable to the invention wherein a plasma receiver is separble.
Figure 15:
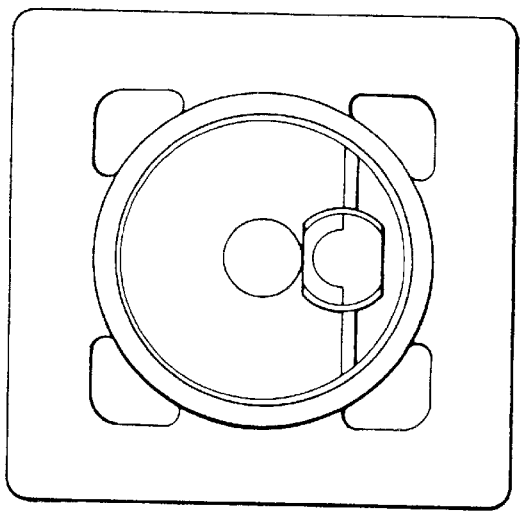
FIG. 15 is a plan view and FIG. 16 is a bottom view thereof.
Figure 16:
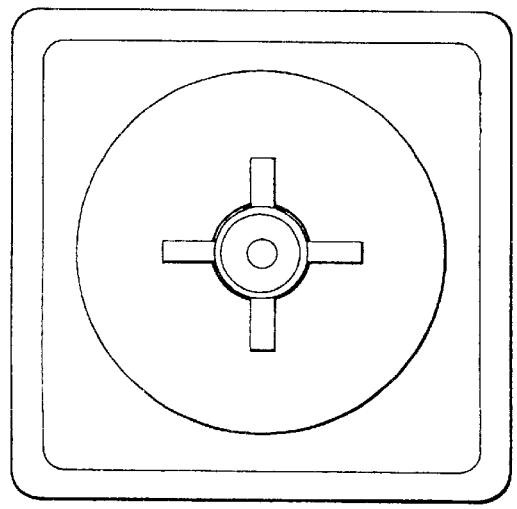

A blood filter unit illustrated in FIGS. 14–16 was prepared. The filter unit was the same as Example 2, except that the filter chamber was made square and that the plasma receiver was separated. The blood filter was used as a plasma-collecting device by attaching the blood-collecting needle illustrated in FIG. 8 or 9. Heparin can be disposed on the inner wall of the filter unit, the filtering material, the plasma receiver, or any other place in the passage of blood or plasma.

Example 4

Figure 17:
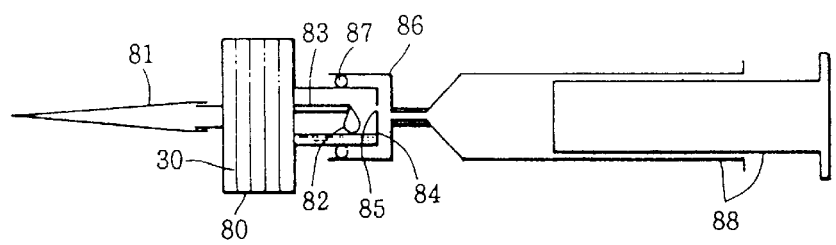
FIG. 17 is a longitudinal section of another plasma-collecting device embodying the invention.
Figure 18:
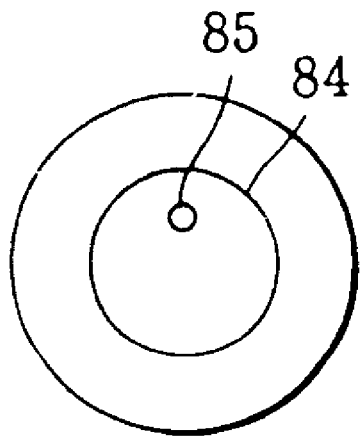
FIG. 18 is a plan view of the blood filter unit.
Figure 19:
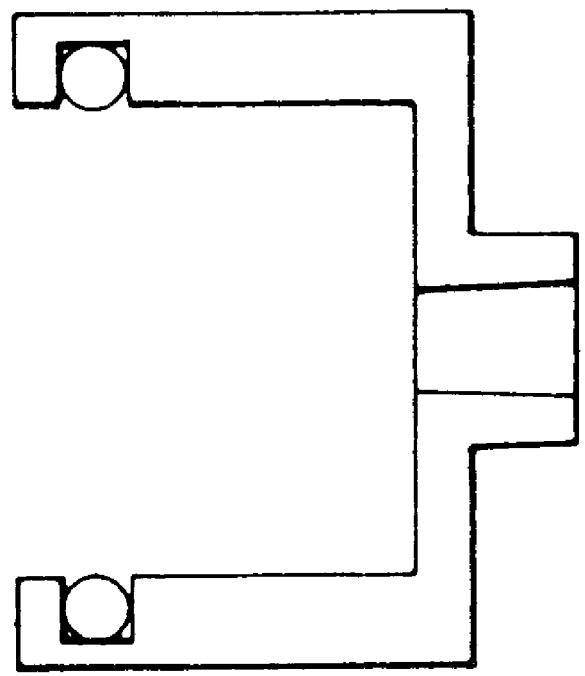
FIG. 19 is a longitudinal section of the adapter for suction used therein.

Another plasma-collecting device illustrated in FIG. 17 was prepared composed of a blood-collecting needle 81, a filter holder 80, an adapter for suction 86 and a syringe 88 for suction. The adapter for suction 86 was a member connecting the syringe 88 to the filter holder 80 in an airtight state, and a rubber O-ring for ensuring airtight conditions was provided on the inner circumferential wall of the adapter 86. FIG. 19 is a section of the adapter 86.

The filter holder 80 had a blood inlet, a filter chamber containing blood filtering material 30, a plasma passage 83. a plasma receiver 82 and a sealing member 84. The sealing member 84 is "sealon" (Fuji Photo Film Co., Ltd.) 300 g in thickness. Instead of the syringe 88 for suction, another suction device, such as a suction pump can be used. The adapter for suction 86 may be not an independent member but a part of the exit of the plasma receiver which has a structure capable of connecting to the syringe for usction or the like directly.

In the plasma-collecting device of FIG. 17, the capacity of the syringe 88 was 10 ml. Upon assembling the blood filter unit, 10 μl of haparin aqueous solution (5 units) was dropped onto the appermost glass fiber filter, and then dried. The blood-collecting needle was inserted into vein according to usual blood collecting manner, and blood was slowly sucked. Plasma not containing blood cells was slowly entered into the plasma receiver. After about seconds, the needle was drawn out from vein to fininsh the blood collection.

The adapter for suction and syringe were detached from the blood filter unit, and then, the plasma receiver was detached. After detaching the sealing member, the plasma receiver was set on the sample holding portion, of which the sampler portion had been reconstructed so as to set the plasma receiver as it is, of an analyzer ("Fuji Dri-Chem 3030", Fuji Photo Film Co., Ltd.), and plasma components were measured.

In comparison, the vein blood was simultaneously collected by a vacuum blood-collecting tube containing heparin according to conventional manner, and the blood was centrifuged to obtain plasma. Concentrations of respective components were measured by a clinical chemistry automatic analyzer ("Hitachi 7150", Hitachi Ltd.).

The results are summarized in Table 1. As can be seen from the table, the difference between the plasma obtained by using the plasma-collecting device of the invention and that obtained by the conventional method was very small, and it was confirmed that the plasma obtained by using the plasma-collecting device of the invention is in the same level as the plasma obtained by the conventional method in the clinical diagnostic viewpoint.

TABLE 1

| | Item | Conventional Plasma | Plasma of Invention | Unit |
|---|---|---|---|---|
| Enzyme | A L P | 164 | 164 | u / L |
| | AMYL | 100 | 99 | u / L |
| | C P K | 119 | 124 | u / L |
| | G G T | 28 | 22 | u / L |
| | G O T | 21.2 | 22.5 | u / L |
| | G P T | 17.8 | 18 | u / L |
| | L D H | 116 | 126 | u / L |
| | L A P | 42 | 40 | u / L |
| | M-MB | 11.2 | 12.7 | u / L |
| End Point Assay | A L B | 4.32 | 4.37 | g / dL |
| | TBIL | 0.54 | 0.51 | mg/ dL |
| | B U N | 13.7 | 13.8 | mg/ dL |
| | C A | 8.7 | 8.9 | mg/ dL |
| | T G | 79 | 82 | mg/ dL |
| | C R E | 0.82 | 0.9 | mg/ dL |
| | TCHO | 159 | 161 | mg/ dL |
| | G L U | 68 | 70 | mg/ dL |
| | T P | 6.89 | 6.7 | g / dL |
| | U A | 5.61 | 5.44 | mg/ dL |

We claim:

1. A plasma-collecting device which comprises a blood filtering material comprising glass fiber filter and microporous membrane, a holder comprising a filter chamber, a plasma receiver, a plasma passage leading from the filter chamber to the plasma receiver and a baffle at an exit of the plasma passage, said filter chamber having a volume of 101 to 200% of the blood filtering material in the dry state and having a blood inlet located on an underside of the filter chamber and a plasma outlet located on an upside of the filter chamber, said filter chamber accommodating the blood filtering material so that the microporous membrane is located on the plasma outlet side, said plasma receiver being located on the upside of the filter chamber, and a blood-collecting needle being connected to the blood inlet.

2. The plasma-collecting device of claim 1 wherein an anticoagulant is provided at least one place in a passage from the blood-collecting needle to the plasma-receiver.

3. The plasma-collecting device of claim 1 wherein plasma outlet side of the blood filtering material is apart from the holder.

4. The plasma-collecting device of claim 1 wherein the plasma receiver is separable from the holder.

5. The plasma-collecting device of claim 1 wherein upper opening of the plasma receiver is sealed by a puncturable sealing member.

6. The plasma-collecting device of claim 1 wherein upper opening of the plasma receiver is sealed by detachable sealing member.

7. The plasma-collecting device of claim 6 wherein the sealing member has a vent hole.

8. The plasma-collecting device of claim 1 wherein the microporous membrane is polysulfone membrane.

* * * * *